United States Patent [19]

Nader

[11] Patent Number: 5,371,291
[45] Date of Patent: Dec. 6, 1994

[54] SYNTHESIS OF 4,6-DIAMINORESORCINOL

[75] Inventor: Bassam S. Nader, Midland, Mich.

[73] Assignee: The Dow Chemical Company, Midland, Mich.

[21] Appl. No.: 137,663

[22] Filed: Oct. 15, 1993

[51] Int. Cl.$^5$ .......................................... C07C 209/36
[52] U.S. Cl. ...................................... 564/418; 562/78; 562/81; 564/443; 568/709; 568/765
[58] Field of Search .................... 562/78, 81; 564/418, 564/443; 568/709, 765

[56] References Cited

U.S. PATENT DOCUMENTS

| | | | |
|---|---|---|---|
| 3,903,178 | 9/1975 | Nakamura et al. | 568/709 |
| 4,038,328 | 7/1977 | Pelster et al. | 568/709 |
| 4,704,469 | 11/1987 | Valle | 560/65 |
| 4,766,244 | 8/1988 | Lysenko | 564/418 |
| 4,982,001 | 1/1991 | Lysenko et al. | 564/418 |

OTHER PUBLICATIONS

"Polybenzothiazoles and Polybenzoxazoles" listed in The Encyclopedia of Polymer Science and Engineering vol. 11 pp. 601–635, © 1988 by John Wiley & Sons, Inc.

"Anthracene Derivatives" by M. V. Gorelik listed in J. Gen. Chem. USSR 1964, 34, p. 2028.

*Primary Examiner*—Richard L. Raymond

[57] ABSTRACT

The invention is a new process for preparing 4,6-diaminoresorcinol, a precursor to polybisbenzoxazoles. The desired product is prepared from resorcinol by incorporating a halo group on the 2-position of resorcinol to form 2-haloresorcinol, then nitrating selectively at the 4- and 6-positions of the 2-haloresorcinol to form 2-halo-4,6-dinitroresorcinol, then hydrogenating the 2-halo-4,6-dinitroresorcinol. The selective incorporation of a halo group on the 2-position of resorcinol is accomplished by sulfonating resorcinol at the 4- and 6-positions. The following scheme illustrates the synthetic route used to prepare 4,6-diaminoresorcinol from resorcinol:

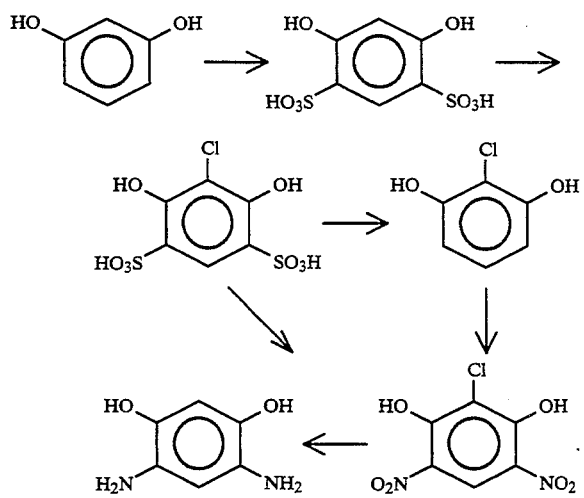

5 Claims, No Drawings 5,371,291

SYNTHESIS OF 4,6-DIAMINORESORCINOL

BACKGROUND OF INVENTION

This invention relates to a process for preparing 4,6-diamino-1,3-benzenediol (4,6-diaminoresorcinol). More specifically, it relates to the synthesis of 4,6-diaminoresorcinol starting with 1,3-benzenediol (resorcinol).

Diaminoresorcinols are useful as monomers for the preparation of polybenzoxazoles (PBOs), the utility of which is discussed by, for example, Wolfe in Mark et al., "The Encyclopedia of Polymer Science and Engineering", vol. 11, pp. 601–635, Wiley-InterScience Publication, New York, 1988. One of the more efficient and economical methods of preparing 4,6-diaminoresorcinol had been Lysenko's process (U.S. Pat. No. 4,766,244, herein incorporated by reference) which reported the synthesis of the desired product in high purities and yields in three steps from 1,2,3-trichlorobenzene.

Unfortunately, halogenated organic compounds—including halogenated arenes—have become the subject of close environmental scrutiny in recent years. Consequently, the once inexpensive and plentiful 1,2,3-trichlorobenzene is becoming expensive and hard to obtain. The questionable long-term availability of 1,2,3-trichlorobenzene requires that an inexpensive commodity starting material be found to prepare 4,6-diaminoresorcinol.

Lysenko et al. addresses this problem somewhat in U.S. Pat. No. 4,982,001, herein incorporated by reference, by preparing 4,6-diaminoresorcinol from the inexpensive and readily available resorcinol through a 1,3-bis(methylcarbonato)benzene intermediate. The steric hindrance of this intermediate causes nitration to take place mostly at the 4- and 6-positions, so that the desired 4,6-diaminoresorcinol can be prepared upon hydrolysis and hydrogenation. Unfortunately, a significant degree of undesirable nitration occurs at the 2-position of the intermediate, making this process impractical.

In view of the deficiencies in the art, it would be desirable to prepare 4,6-diaminoresorcinol from resorcinol by a process where undesirable nitration does not occur.

SUMMARY OF INVENTION

The present invention is a process which comprises reacting a 2-haloresorcinol with a nitrating agent under such conditions to form a 2-halo-4,6-dinitroresorcinol.

A further aspect of this invention is that it is a process which comprises reacting a 2-haloresorcinol-4,6-disulfonic acid with a desulfonating nitrating agent under such conditions to form a 2-halo-4,6-dinitroresorcinol.

A further aspect of this invention is that it is a process for preparing 4,6-diaminoresorcinol comprising the steps of:

a) incorporating protecting substituents at the 4- and 6-positions of resorcinol to form a 4,6-disubstituted resorcinol; then b) reacting the 4,6-disubstituted resorcinol with a halogenating agent to form a 2-halo-4,6-disubstituted resorcinol; then c) removing the protecting substituents at the 4-and 6-postions of the 2-halo-4,6-disubstituted resorcinol to form the 2-haloresorcinol; then d) simultaneously with or after step (c), nitrating the 2-haloresorcinol to form a 2-halo-4,6-dinitroresorcinol; then e) hydrogenating the 2-halo-4,6-dinitroresorcinol to form 4,6-diaminoresorcinol.

The present invention addresses the problems associated with 1,2,3-trichlorobenzene by preparing 4,6-diaminoresorcinol from resorcinol—an inexpensive, readily available, and environmentally acceptable alternative—and through a synthetic route heretofore unknown.

DETAILED DESCRIPTION OF INVENTION

In one aspect of this invention, diaminoresorcinol is prepared from resorcinol by way of reduction of a resorcinol that has been selectively nitrated at the 4- and 6-positions and halogenated at the 2-position. This selective nitration is accomplished subsequent to the addition of a halo group to the 2-position of resorcinol.

This halo group addition is carried out by first incorporating protecting substituents on the 4- and 6-positions, then halogenating at the 2-position of resorcinol. A protecting substituent is one that protects the resorcinol from undesirable chlorination at the 4- and 6-positions, but does not inhibit nitration at these positions. Preferably, halo group incorporation at the 2-position is carried out through sulfonating at the 4- and 6-positions, then halogenating at the 2-position, then optionally protodesulfonating at the 4- and 6-positions of resorcinol. (See Valle et al., U.S. Pat. No. 4,704,469, herein incorporated by reference.) Suitable sulfonating reagents include fuming sulfuric acid containing about 10 mol % to about 20 mol % free $SO_3$, or sulfuric acid with a concentration between about 90% and about 98% w/w in water. At least 2 mole equivalents of the sulfonating reagent is used per mole equivalent of resorcinol. The sulfonation reaction to form the intermediate resorcinol-4,6-disulfonic acid is advantageously carried out at a temperature ranging from about 5° C. to about 120° C., preferably ranging from about 60° C. to about 110° C., until sulfonation is substantially complete, preferably for between about 30 minutes to about 4 hours, more preferably about 2 hours.

The resorcinol-4,6-disulfonic acid is halogenated to form a second intermediate, a 2-haloresorcinol-4,6-disulfonic acid. This halogenation step is carried out prior to the nitration step to prevent the undesirable formation of the highly explosive styphnic acid (2,4,6-trinitroresorcinol). Any halogenating agent that adds a halo group to a phenolic compound may be used. The halogenating agents may be fluorine, chlorine, bromine, and iodine; preferably bromine and chlorine; and more preferably chlorine. Reagents that easily liberate chlorine or bromine in situ, such as a dilute hydrogen halide and an oxidizing reagent in an aqueous medium are preferred. For example, a mixture of dilute hydrochloric acid and an aqueous solution of an alkaline chlorate favor chlorine liberation, and a mixture of dilute hydrobromic acid and an aqueous solution of an alkaline bromate favor bromine liberation. The preferred concentration of aqueous dilute hydrogen halide is between about 5% and about 25% v/v. The preferred temperature range is between about −5° C. and about 25° C.

It is also possible to chlorinate or brominate resorcinol-4,6-disulfonic acid using free halogens in nonaqueous solvents that do not react with the halogens. Suitable solvents include, but are not restricted to, nitrobenzene, dimethylformamide, carbon tetrachloride, methylene chloride, and sulfuric acid, or mixtures thereof. Small quantities of water, preferably not exceeding 8% w/w, may also be present in the reaction medium. The reaction is preferably carried out at temperatures less than 30° C., more preferably between about 5° C. and about 25° C. The 2-haloresorcinol-4,6-disulfonic acid is preferably 2-chlororesorcinol-4,6-disulfonic acid or 2-bromoresorcinol-4,6-disulfonic acid, more preferably 2-chlororesorcinol-4,6-disulfonic acid.

The 2-haloresorcinol-4,6-disulfonic acid can either be converted directly to a 2-halo-4,6-dinitroresorcinol or protodesulfonated to a 2-haloresorcinol, which also serves as a precursor to the 2-halo-4,6-dinitroresorcinol. The following discussion is directed first to the conversion of the 2-haloresorcinol-4,6-disulfonic acid to the 2-haloresorcinol, and the conversion of the 2-haloresorcinol to the 2-halo-4,6-dinitroresorcinol. Thereafter, the direct conversion of the 2-haloresorcinol-4,6-disulfonic acid to the 2-halo-4,6-dinitroresorcinol is discussed.

The 2-haloresorcinol-4,6-disulfonic acid is protodesulfonated (hydrolyzed) to form a 2-haloresorcinol by the action of an aqueous acid at temperatures varying between about room temperature and about 150° C. Preferred acids are mineral acids, such as aqueous solutions of between about 20% w/w and about 40% w/w sulfuric acid, or about 36% w/w hydrochloric acid; dilute organic acids, such as trifluoroacetic acid or monochloroacetic acid; sulfonic or monocyclic aromatic acids, such as aqueous p-toluenesulfonic acid at concentrations of about 20% w/w to about 90% w/w. Completion of protodesulfonation depends on reaction temperature and may vary from about 1 to about 24 hours.

The 2-haloresorcinol obtained from the protodesulfonation reaction may be isolated by known procedures such as extraction with organic solvents. Suitable solvents are those that dissolve the 2-haloresorcinol but that are substantially immiscible with the inorganics, such as methylene chloride. The 2-haloresorcinol may be purified by, for example, flash chromatography using methylene chloride as eluent. This purification step is effective in separating the 2-haloresorcinol from any unreacted resorcinol, which, as mentioned previously, forms styphnic acid upon nitration. The 2-haloresorcinol can be synthesized from resorcinol without isolation of either the resorcinol-4,6-disulfonic acid or the 2-haloresorcinol-4,6-disulfonic acid.

The 2-haloresorcinol is preferably 2-bromoresorcinol or 2-chlororesorcinol, and more preferably 2-chlororesorcinol.

Any nitrating agent which will nitrate the 2-haloresorcinol at the 4- and 6-positions under the reaction conditions described herein can be used to convert the 2-haloresorcinol to the 2-halo-4,6-dinitroresorcinol. Suitable nitrating agents include alkali metal nitrates, such as sodium and potassium nitrate; and nitric acid at various concentrations, such as fuming nitric acid and concentrated nitric acids. Concentrated nitric acid, e.g., from about 60 to about 75 weight percent nitric acid, especially about 70 weight percent, is the most preferred nitrating agent.

Any acid which, in the presence of nitric acid, will facilitate the formation of nitronium ions under the reaction conditions described herein can be used in the nitration step of the present process. Suitable acids for this purpose include trifluoroacetic acid, hydrochloric acid, and sulfuric acid, with hydrochloric acid being preferred and sulfuric acid being most preferred.

Suitable molar ratios of nitrating agent to 2-haloresorcinol are those sufficient to cause the substitution of 2 nitro groups per molecule of 2-haloresorcinol. The nitrating agent is generally used in stoichiometric excess, though the degree of excess does not appear to be critical. Typical molar ratios of acid, preferably sulfuric acid, to 2-haloresorcinol are in the range from about 8:1 to about 20:1, with about 10:1 to about 15:1 being more preferred. The most preferred ratio is about 10:1.

The nitration of 2-haloresorcinol is found to be quite rapid, probably because the hydroxy groups of these compounds are strong promoters of electrophilic aromatic substitution. Consequently, it is advantageous to control the temperature of the nitration reaction and the rate of addition of the nitrating reagent to minimize the formation of undesirable byproducts. In a preferred embodiment of the nitration of 2-haloresorcinol, a mixture of nitric acid and sulfuric acid is added to a homogeneous mixture of 2-haloresorcinol and sulfuric acid at a rate appropriate to control the resultant exotherm, and to minimize the formation of side products. The temperature of this reaction is preferably between about −10° C. and about 20° C., more preferably between about 0° C. and about 15° C. The pressure of the nitration step can be any pressure at which nitration will occur. Preferred pressures are about atmospheric, although subatmospheric or superatmospheric pressures can be employed.

The 2-halo-4,6-dinitroresorcinol produced by this step can be isolated by conventional precipitation and filtration techniques and is typically obtained in greater than 95 percent purity, preferably greater than 98 percent purity and most preferably greater than about 99.9 percent purity.

As mentioned previously, it is also possible to prepare the 2-halo-4,6-dinitroresorcinol directly from the 2-haloresorcinol-4,6-disulfonic acid. In this procedure, the 2-haloresorcinol-4,6-disulfonic acid— prepared as described previously, and advantageously separated from any components that may react undesirably with the nitrating agent—is desulfonated and nitrated in one step.

In direct nitration, the 2-haloresorcinol-4,6-disulfonic acid can be combined with a mild base, such as sodium bicarbonate, at a rate and temperature sufficient to control the resulting exotherm, and at such a concentration to make the media nonacidic. Then, the nitrating agent, preferably concentrated aqueous nitric acid, more preferably about 70 weight percent nitric acid, can be added at a rate and a temperature sufficient to control the resulting exotherm. Stirring of the reaction mixture is advantageously continued until the nitration reaction is substantially complete, after which time the product 2-halo-4,6-dinitroresorcinol can be isolated by, for example, filtration.

Alternatively, desulfonation and nitration can be done using aqueous nitric acid and a small amount of sodium nitrite. (See Gorelik, J. Gen. Chem USSR, 34, 2028, (1964), herein incorporated by reference).

If desired, this compound may be further purified by means such as recrystallization from an appropriate solvent, such as ethanol. However, whether prepared from the 2-haloresorcinol or the 2-haloresorcinol-4,6-disulfonic acid, the 2-halo-4,6-dinitroresorcinol can generally be used in the hydrogenation step of the present invention without further purification.

The hydrogenation step of the present invention involves contacting the 4,6-dinitro-2-haloresorcinol with a hydrogenating agent. The hydrogenating agent can be any material which will supply hydrogen to the reaction. Suitable hydrogenating agents include hydride reducing agents, such as lithium aluminum hydride; dissolving metal reducing agents in protic solvents, such as sodium amalgam in ethanol; and hydrogen over a catalyst. Of the hydrogenating agents, hydrogen over a catalyst is preferred. More preferably, the reduction step involves contacting the 4,6-dinitro-2-haloresorcinol with hydrogen over a catalyst in the presence of a solvent.

The solvent is one that remains unreactive under the hydrogenation conditions. Suitable solvents include alcohols, such as ethanol, methanol and propanol; alkylene glycols, such as ethylene glycol; and carboxylic acids, such as acetic acid, with carboxylic acids being preferred. The preferred carboxylic acid is acetic acid.

Useful hydrogenation catalysts include materials that contain a noble metal and will catalyze the reduction of the nitro groups of and the elimination of the halogen from the 2-halo-4,6-dinitroresorcinol. Examples of suitable catalysts include noble metals on carbon, noble metal oxides and noble metals supported on alkaline earth carbonates. Noble metals herein refer to gold, silver, platinum, palladium, iridium, rhodium, mercury, ruthenium and osmium. Preferred catalysts include palladium-on-carbon, platinum-on-carbon and platinum oxide.

The catalyst is employed in an amount sufficient to catalyze the conversion of starting material in the presence of a hydrogenating agent to the corresponding diaminoresorcinol. Typically, from about 0.001 to about 1 molar equivalents of catalyst per equivalent of the initial concentration 2-halo-4,6-dinitroresorcinol are used. Preferably, from about 0.01 to about 0.5 and most preferably from about 0.01 to about 0.1 molar equivalents of the initial concentration of 2-halo-4,6-dinitroresorcinol are used.

Suitable concentrations of 2-halo-4,6-dinitroresorcinol in the reaction medium are those sufficient to afford an efficient recovery of product. Examples of such suitable concentrations are those in the range from about 0.001 to about 10 molar, with from about 0.01 to about 5 molar being preferred.

The amount of hydrogenating agent used in the reduction step is an amount sufficient to convert 2-halo-4,6-dinitroresorcinol to 4,6-diaminoresorcinol. In general, a large excess of the hydrogenating agent is used to enhance the reaction rate. Suitable amounts include those in the range from about 200 to about 2000 mole percent based on moles of the 2-halo-4,6-dinitroresorcinol, and preferably from about 500 to about 1000 mole percent. The temperature in the hydrogenation step is sufficient to effect completion of the hydrogenation reaction. Preferably, the temperature is in the range from about 0° C. to about 150° C., more preferably from about 30° C. to about 75° C. Pressures employed are suitably from about 1000 psi to about 1 psi, more preferably from about 400 psi to about 2 psi.

The 4,6-diaminoresorcinol can be recovered using known recovery methods such as precipitation and filtration. The product is generally isolated and stored as a hydrohalide salt advantageously mixed with an antioxidant, such as $SnCl_2$, to prevent oxidative decomposition. It is also common practice to isolate the product as a salt of a mineral acid such as sulfuric, nitric, or phosphoric acid. The 4,6-diaminoresorcinol of the present invention is typically obtained in a purity greater than 98 weight percent, preferably greater than 99 weight percent, most preferably greater than 99.9 weight percent, with yields being typically greater than 80 mole percent, preferably greater than 85 mole percent and most preferably greater than 95 mole percent, based on moles of the 2-halo-4,6-dinitroresorcinol charged to the reaction.

The 4,6-diaminoresorcinol is used to make polybisbenzoxazoles (PBOs), polymers which can be used in applications such as insulators, solar arrays, and tear-resistant gloves. (See Wolfe, supra.)

EXAMPLE 1

A. Preparation of 2-Chlororesorcinol

Into a 500 mL flask containing 156 mL of 96% (w/w) sulfuric acid are added 52.5 g of resorcinol. Before the resorcinol completely dissolves, another 156 mL of 96% (w/w) sulfuric acid and another 52.5 g of resorcinol are added. The resulting exotherm causes the temperature of the mixture to increase to as much as 90° C. When this the temperature is reached, or when the temperature of the mixture no longer increases, the mixture is heated to 110° C. for two hours. Then, the mixture is cooled to 15° C., after which time 120 g of chlorine are added at such a rate to maintain a temperature of 15° C. The mixture is then poured into a 2 liter flask containing 450 g of ice and 400 mL of water. To the resulting aqueous phase is added aqueous sodium hydroxide (prepared by dissolving 76 g of sodium hydroxide into 150 mL of water) followed by a 24-hour reflux of the mixture. The temperature of the solution is reduced to room temperature, and after extraction by ethyl ether and ether evaporation, the residual mixture, which contains resorcinol and 2-chlororesorcinol, is subjected to flash column chromatography, using $CH_2Cl_2$ as eluent. This affords 29 g (21% yield) of the pure 2-chlororesorcinol (M.P. 97° C.).

B. Preparation of 2-Chloro-4,6-dinitroresorcinol

2-Chlororesorcinol (0.36 g, 2.5 mmol) is placed in a flask which is chilled in an ice-water bath. Concentrated sulfuric acid (5 g) is added slowly with stirring so as not to allow the mixture to warm up. After the 2-chlororesorcinol is dissolved, a premixed solution of $HNO_3$ (70%, 0.9 g, 10 mmol) in concentrated sulfuric acid (5 g) is added dropwise with rapid stirring at such a rate that the temperature does not exceed 15° C. After 20 minutes, the mixture is carefully poured into ice-water (30 mL) with stirring. The solid that separates is collected by filtration and washed with water. Air drying affords 2-chloro-4,6-dinitroresorcinol in sufficient purity—as determined by high performance liquid chromatography, gas chromatography-mass spectrometry, and proton and carbon NMR spectroscopy—that further purification is not needed. The yield is 65%.

C. Preparation of 4,6-Diaminoresorcinol Dihydrochloride

A one-liter Hastalloy C autoclave equipped with a gas dispersion stirrer and cooling coil is charged with 117.3 g (0.5 mole) of 2-chloro-4,6-dinitroresorcinol, 400 ml of glacial acetic acid, 41 g (0.5 mole) of NaOAc, 7.0 g of 10 percent palladium over carbon and 100 mL of $H_2O$. The sealed reactor is charged with 400 psi of $H_2$ and the temperature is brought to 40° C. and maintained between 40° C. and 50° C. during the course of the reaction. After a brief induction period, the uptake of hydrogen becomes extremely rapid and $H_2$ pressure is maintained between 100–400 psi during the reaction. Upon completion, no further uptake of $H_2$ is observed.

The reactor is cooled to room temperature, opened and 400 mL of concentrated HCl containing 10 g of $SnCl_2.2H_2O$ is added to the reaction mixture. The crude product with the catalyst is isolated by filtration. This material is dissolved in 200 g of $H_2O$ at 85° C. and the catalyst is removed by filtration. $H_2O$ (100–300 mL) is added to the filtrate along with 500 mL of HCl and the catalyst-free material is precipitated from the brown solution. Recrystallization is carried out in the existing solvent or the semi-pure material can be isolated and air dried to afford 100 g of crude diaminoresorcinol dihydrochloride, (96.8 mole percent yield based on the 2-chloro-4,6-dinitroresorcinol.

EXAMPLE 2

Direct Nitration of 2-Chlororesorcinol-4,6-disulfonic Acid to 2-Chloro-4,6-dinitroresorcinol To a stirred solution of 2-chlororesorcinol-4,6-disulfonic acid (0.5 g, 1.6 mmol) in water (10 mL) is added sodium bicarbonate (0.55 g, 6.5 mmol) at such a rate that the resulting gas evolution remains under control. When the gas evolution has subsided, the mixture is heated in a bath maintained at 80° C., and nitric acid (70% w/w in water, 3.5 mL, 39 mmol) is added slowly over 2 minutes. Upon completion of the nitric acid addition, the reaction mixture is heated to reflux for 5 minutes and allowed to cool. The solid that separates is isolated by filtration, washed with a small amount of ice-cold water, and allowed to dry. This affords 0.24 g (63% yield) of 2-chloro-4,6-dinitroresorcinol as a yellow solid, which can be used without further purification for the subsequent reduction reaction.

What is claimed is:

1. A process for preparing 4,6-diaminoresorcinol comprising the steps of:
   a) incorporating protecting substituents at the 4- and 6-positions of resorcinol to form a 4,6-disubstituted resorcinol; then
   b) reacting the 4,6-disubstituted resorcinol with a halogenating agent to form a 2-halo-4,6-disubstituted resorcinol; then
   c) removing the protecting substituents at the 4-and 6-positions of the 2-halo-4,6-disubstituted resorcinol to form the 2-haloresorcinol;
   d) simultaneously with or after step (c), nitrating the 2-haloresorcinol to form a 2-halo-4,6-dinitroresorcinol; and then
   e) hydrogenating the 2-halo-4,6-dinitroresorcinol to form 4,6-diaminoresorcinol.

2. The process of claim 1 wherein the hydrogenating agent is hydrogen over a catalyst.

3. The process of claim 1 wherein the protecting substituents are sulfonic acid groups.

4. The process of claim 3 wherein the halogenating agent is chlorine or bromine.

5. The process of claim 4 wherein the nitrating agent is a mixture of nitric acid and sulfuric acid.

* * * * *